(12) United States Patent  (10) Patent No.: US 8,273,065 B2
Gill et al.  (45) Date of Patent: Sep. 25, 2012

(54) OSTOMY BAG ODOR CONTROL AND IRRIGATION SYSTEM

(76) Inventors: Zora Singh Gill, Bakersfield, CA (US); Nichater Singh Gill, Bakersfield, CA (US)

( * ) Notice: Subject to any disclaimer, the term of this patent is extended or adjusted under 35 U.S.C. 154(b) by 58 days.

(21) Appl. No.: 13/035,866

(22) Filed: Feb. 25, 2011

(65) Prior Publication Data

US 2011/0196323 A1    Aug. 11, 2011

Related U.S. Application Data

(63) Continuation-in-part of application No. 12/387,360, filed on May 1, 2009, now Pat. No. 7,918,836.

(51) Int. Cl.
 *A61F 5/44* (2006.01)
(52) U.S. Cl. ........ 604/333; 604/332; 604/334; 604/335; 604/337; 604/339; 604/340; 604/341
(58) Field of Classification Search ................... 604/333, 604/334
See application file for complete search history.

(56) References Cited

U.S. PATENT DOCUMENTS

| | | | | |
|---|---|---|---|---|
| 2,887,109 A * | 5/1959 | Barrington | ...................... | 604/92 |
| 4,180,072 A * | 12/1979 | Sneider | ........................... | 604/32 |
| 4,211,224 A * | 7/1980 | Kubach et al. | ................ | 604/333 |
| 4,319,569 A * | 3/1982 | Hu | ................... | 604/32 |
| 4,654,037 A * | 3/1987 | Fenton | ......................... | 604/334 |
| 4,810,250 A * | 3/1989 | Ellenberg et al. | ............. | 604/277 |
| 4,938,750 A * | 7/1990 | Leise, Jr. | ....................... | 604/333 |
| 5,573,187 A * | 11/1996 | Proctor | ........................ | 239/532 |
| 5,860,959 A * | 1/1999 | Gent | ............................ | 604/332 |
| 6,007,525 A * | 12/1999 | Martell | ........................ | 604/333 |
| 6,129,716 A * | 10/2000 | Steer | ............................ | 604/333 |
| 6,165,159 A * | 12/2000 | Blanton | ........................ | 604/333 |
| 6,224,581 B1 * | 5/2001 | Withers et al. | ................ | 604/334 |
| 6,656,169 B1 * | 12/2003 | Steer | ............................ | 604/333 |
| 7,918,836 B2 * | 4/2011 | Gill et al. | ....................... | 604/333 |
| 2003/0073974 A1 * | 4/2003 | Falconer | ....................... | 604/514 |
| 2006/0111682 A1 * | 5/2006 | Schena et al. | ................ | 604/334 |
| 2006/0155252 A1 * | 7/2006 | Walker et al. | ................ | 604/334 |

* cited by examiner

*Primary Examiner* — Tatyana Zalukaeva
*Assistant Examiner* — Ginger T Chapman
(74) *Attorney, Agent, or Firm* — James M. Duncan, Esq.; Klein, DeNatale, Goldner, et. al.

(57) ABSTRACT

An improved ostomy bag comprises an outwardly facing irrigation line attachment adapter. A removable vent housing may be attached to the attachment adapter, where the vent housing is attached during normal operation of the ostomy bag, where the vent housing may comprise a charcoal filter and a scent absorbing medium for reducing odors which may vent from the ostomy bag. The vent housing is attached with quick-connect connectors, and is easily removed so that a conduit may be attached to the attachment adapter, where the conduit is attached to a source of flushing liquid, such as a squeezable reservoir or faucet.

14 Claims, 4 Drawing Sheets

OSTOMY BAG ODOR CONTROL AND IRRIGATION SYSTEM

CROSS-REFERENCE TO RELATED APPLICATIONS

U.S. application Ser. No. 12/387,360 for this invention was filed on May 1, 2009, for which application these inventors claim domestic priority, and which is incorporated in its entirety for this Continuation-in-Part Application.

BACKGROUND OF THE INVENTION

The disclosed device generally relates to devices used for ostomy appliances, and specifically to ostomy appliances having an integral cleaning system, such as colostomy appliances, ileostomy appliances, and urostomy appliances.

In many cases a consequence of surgery for diseases in the gastrointestinal tract is that the colon has been surgically exposed, and the patient is left with an abdominal stoma. The effluents or waste products of the body conveyed through the gastrointestinal tract are discharged through this artificial orifice or opening, and are collected in a collection bag, which is usually adhered to the skin by means of an adhesive wafer or plate having an inlet opening for accommodating the stoma.

Ostomy appliances are well known. Such appliances may be two-piece or one-piece appliances. In both types of appliances, an adhesive barrier member, or base plate, is attached to the wearer. In the case of a one-piece appliance, a receiving member or bag is attached to the base plate. In the case of a two-piece appliance, the adhesive barrier member forms part of a body side member and a receiving member or bag is releasably attached to the body side ostomy member for receiving wastes from the stoma. When using one-piece appliances, the whole appliance, including the adhesive skin barrier securing the appliance to the skin is normally removed and replaced by a fresh appliance. When using two-piece appliances, the body side ostomy member is left in place up to several days, and only the receiving member or bag attached to the body side member is replaced. The attachment means for attaching an ostomy receiving bag may be matching coupling rings or matching flanges and adhesive surfaces engaging with and sealing against a flange area of the body side member.

The presently disclosed ostomy bag overcomes several shortcomings of the prior ostomy bags. The disclosed ostomy bag protects the stoma area from significant contact with excreted wastes and any digestive fluids contained within the wastes, and limits the duration of time the wastes are in contact with the stoma. Exposure of the stoma to fluids, and especially to the corrosive attack from stomach acid, causes pain to the wearer. Cleaning of the known bags can be problematic because a complete flushing of the bag may be difficult to achieve without removal of the bag from the body side member, and the increased risk of spillage caused by removal. Odor is a problem with most of the known bags because of the inability to completely cleanse the bag in place as well as the inability to effectively vent and filter accumulated flatus. Connection of irrigation devices to the known bags can be difficult, and unpleasant odors can be released while the irrigation line is connected to the device.

SUMMARY OF THE INVENTION

Embodiments of the disclosed ostomy bag may comprise either a single chamber or multiple chambers, such as an outer chamber and an inner chamber. In the multiple chamber embodiment, the outer chamber may comprise an upper portion and a lower portion, wherein the upper portion is defined as the section adjacent to the inner chamber and the lower portion is defined as the section extending below the bottom edge of the inner chamber. The upper portion further comprises an entrance from the stoma to the ostomy bag, and the lower portion is where the excreted bodily wastes are stored for eventual disposal. The fit between the outside surface of the inner chamber and the inside surface of the outer chamber is preferably sized for tight clearance to prevent waste from the lower portion from invading the space between the upper portion and the inner chamber. An interference fit is further provided by the "bellowing" out of the bottom of the inner chamber caused by the biasing member described below.

The inner chamber may comprise a one-way valve that allows entry of wastes into the lower portion of the outer chamber but limits the back flow of the bodily wastes from re-entering the inner chamber. The one-way valve may comprise a biasing member attached to opposing sides of the bottom of one of the walls of the inner chamber. The biasing member may have a length L1 that is greater than the inner chamber bottom wall length L2. The bottom of the inner chamber is urged shut by the force exerted by the biasing member on the bottom of the inner chamber wall.

The disclosed ostomy bag also provides an improved means for cleaning the bag, thereby increasing comfort and convenience to the wearer, and reducing the likelihood that unpleasant odors will be vented during the cleaning operation. The bag may comprise an irrigation system that links to an external fluid source and provides for the flushing of both the inner chamber and the outer chamber simultaneously. The irrigation system may comprise an irrigation connector adapter affixed to the outer chamber and an attachment adapter attached to the inner chamber. The attachment adapter may be attached to the irrigation connector adapter, and the irrigation tube.

The irrigation tube, which is closed ended, may be routed through a first slit and a second slit that extend through the inner chamber. The irrigation tube may comprise slits along the portion of the irrigation tube disposed within the inner chamber and through a large part of the outer chamber. The flushing or rinsing liquid may be introduced into the irrigation tube from a water supply means such as a squeezable reservoir.

The ostomy bag may comprise a vent contained within a vent housing placed at the upper portion of the outer chamber, and the vent may be used to vent flatus and associated odors that collect within the bag during normal digestion. The vent provides for a slow release of flatus that would otherwise collect in the ostomy bag and cause uncomfortable pressure to the wearer, or exude from the bag when emitted. The vent housing may further comprise a charcoal filter to strip the noxious smells from the vented flatus. In addition, the vent housing may comprise scent storage means, such as a tissue sponge, etc., to which scents may be added. The vent housing may have a quick-connect/release connector allowing the vent to be easily attached and remove to the irrigation connector adapter.

DETAILED DESCRIPTION OF THE INVENTION

Figure 1:
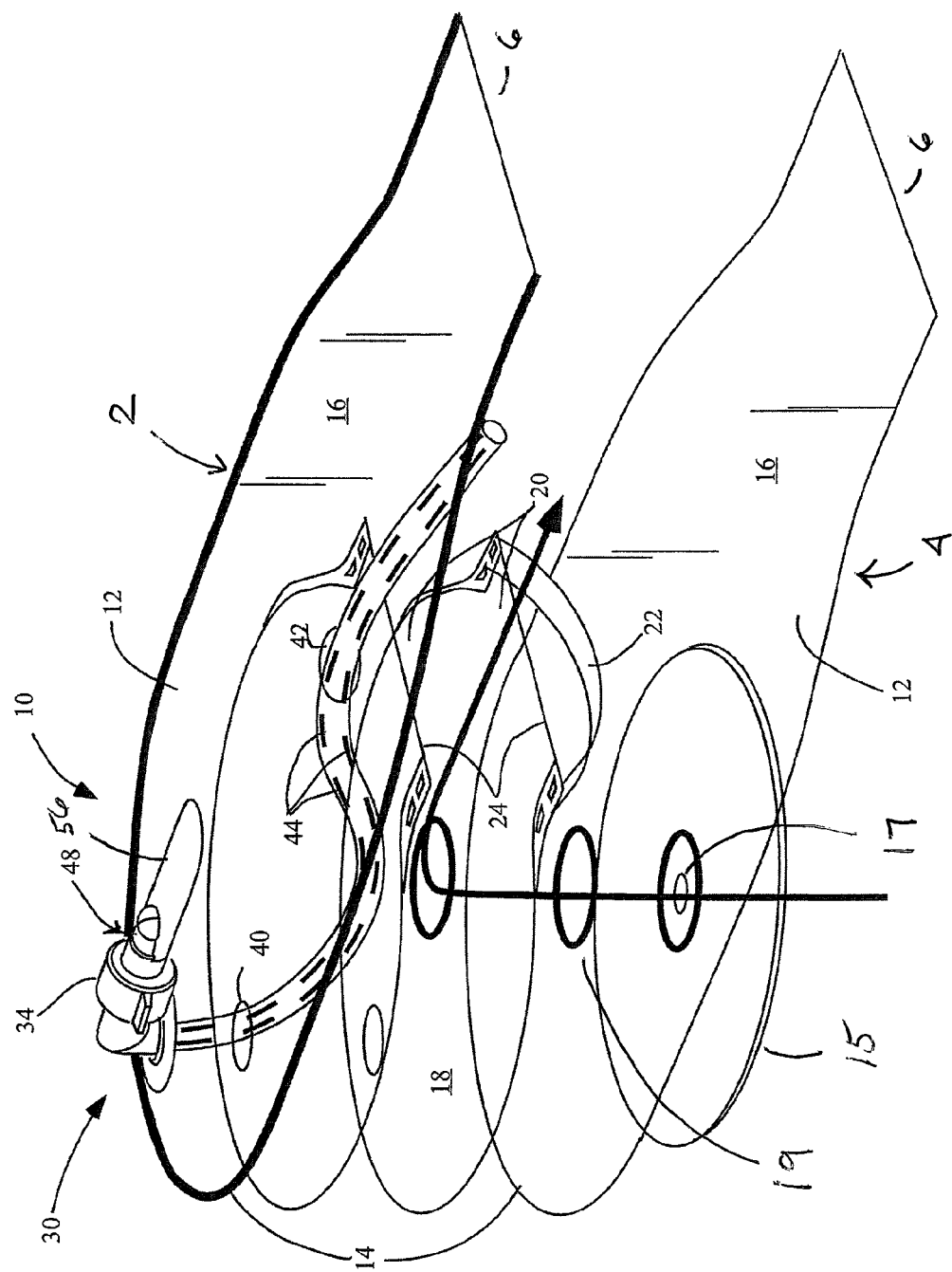
FIG. 1 shows an exploded view of an embodiment of the presently disclosed filter-connector system as attached to an ostomy bag.

Referring now to the Figures, FIGS. 1 through 6 depict various views of an embodiment of an ostomy bag utilizing different embodiments of the disclosed connector 34 and vent housing 48. While a variety of different ostomy bags may be equipped with the disclosed connector 34 and vent housing 48, the inventors herein have invented an ostomy bag 10 which may be utilized in combination with the disclosed connector 34 and vent housing 48, which are an improvement to the known ostomy bags. The disclosed connector 48, vent housing 48, and irrigation storage and connection conduit comprise an ostomy bag odor control and irrigation system An embodiment of an ostomy bag 10 which may be utilized with the connector 34 and vent housing 48 and ostomy bag odor control and irrigation system is shown in FIG. 1. For this embodiment, the ostomy bag comprises a front member 2 and a rear member 4, which are fused together along the edges, except for the bottom edges 6, which define a waste disposal opening when the front member 2 is fused with the rear member 4. The ostomy bag 10 may further comprise an outer chamber 12 and an inner chamber 18, wherein the inner chamber 18 is disposed within the outer chamber 12. The outer chamber further comprises an upper portion 14 defined as the section adjacent to the inner chamber 18, and a lower portion 16 defined as the section extending below the bottom edge of the inner chamber 18. The upper portion 14 comprises a reinforcement member 15 comprising an opening 17 through which waste from the stoma to enter the ostomy bag 10 through opening 19 in the rear member 4. The lower portion 16 is where the excreted bodily wastes are stored for eventual disposal through a discharge opening, which is defined at bottom edges 6. Bottom edges 6 may be closed by rolling or folding the edges together and temporarily fastening with a clip (not shown). The flow of waste into the ostomy bag 10 is generally depicted in FIG. 1 by the directional arrow.

For the embodiment of the colostomy bag 10 depicted in the Figures, the inner chamber 18 may comprise a one-way valve 20 that allows entry of wastes into the lower portion 16 of the outer chamber 12 but limits the back flow of the bodily wastes from the lower portion 16 of the ostomy bag 10 back into the inner chamber 18. The one-way valve 20 allows free passage of wastes into the lower portion 16 for storage. The one-way valve 20 may comprise a biasing means, such as biasing member 22 attached to opposite sides of one of the walls of the inner chamber 18. The biasing member 22 may have a length that is longer then the length of the bottom 24 of the inner chamber 18 walls. As the biasing member's 22 length L1 is greater than the inner chamber bottom side 24 length L2, the bottom 24 of the inner chamber 18 is urged shut by the force exerted by the biasing member 22 on the bottom 24 of the inner chamber 18. This urging action enhances the one-way valve 20 such that bodily wastes are readily admitted through the valve 20 from the inner chamber 18 to the lower portion 16 for storage, but the reverse is not true. Waste does not flow from the lower portion 16 back into the inner chamber 18. In addition, waste does not readily flow from the lower portion 16 to the upper portion 14, as the biasing member 22 creates an additional barrier against upwards flow from the storage area to the inlet area.

Figure 2:
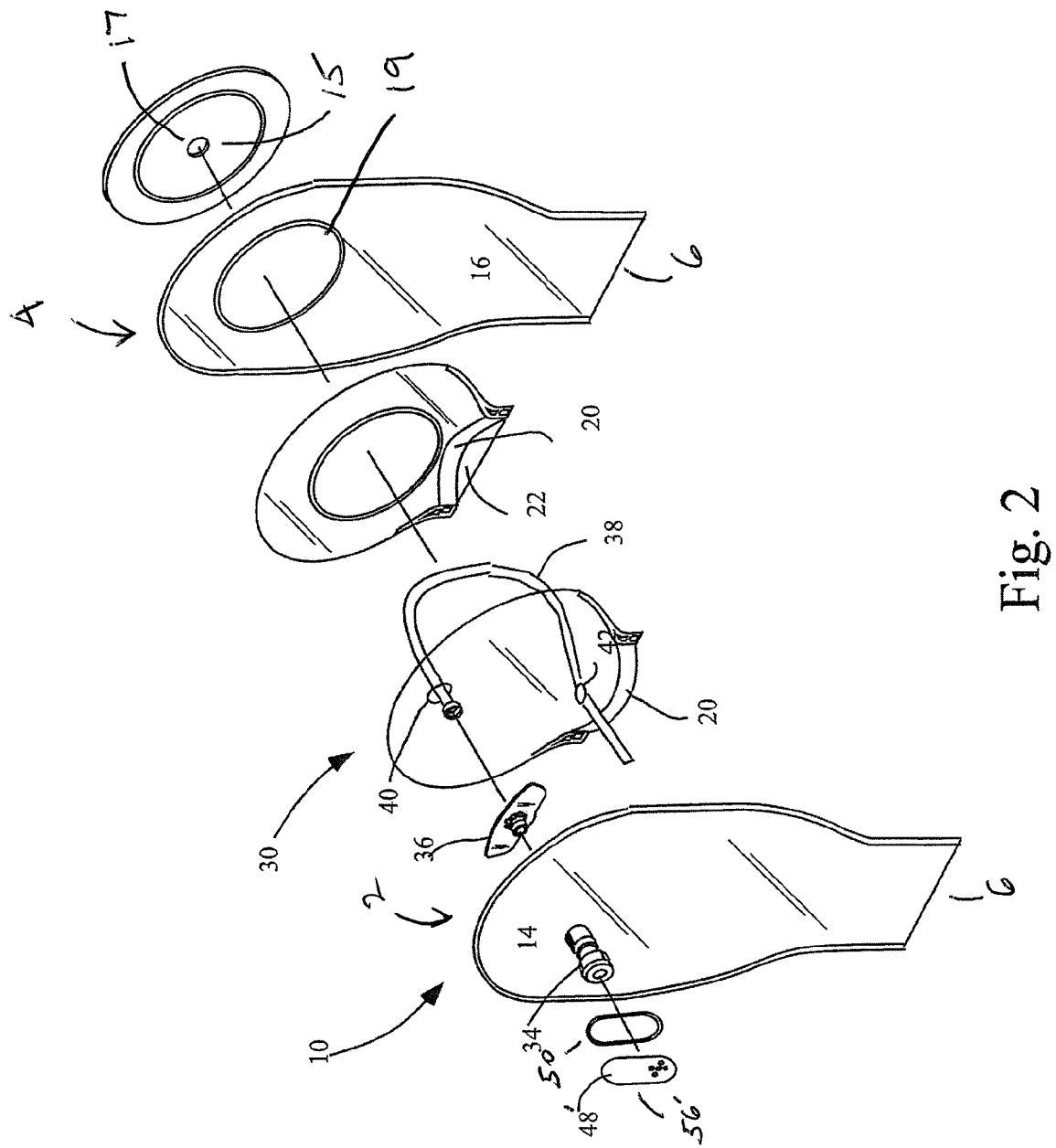
FIG. 2 shows an exploded view of an embodiment of an ostomy bag with a cleaning system and an embodiment of the presently disclosed filter-connector system.
Figure 5:
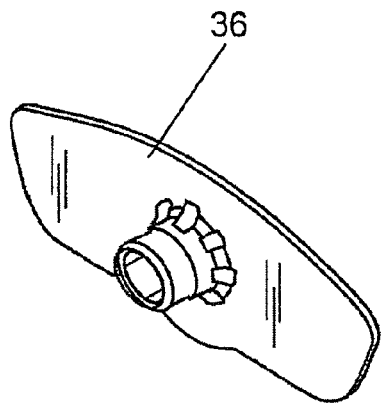
FIG. 5 shows a perspective view of an embodiment of an attachment adapter.
Figure 6:
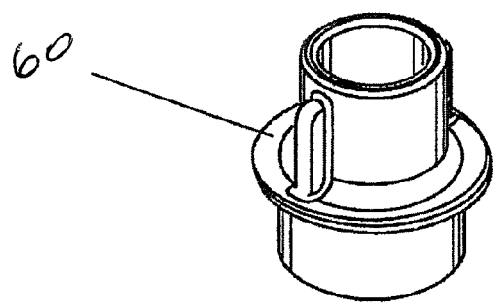
FIG. 6 shows a perspective view of an embodiment of a quick connect coupling which may be utilized to attach either the filter housing or an irrigation conduit to the attachment adapter shown in FIG. 5.
Figure 7:
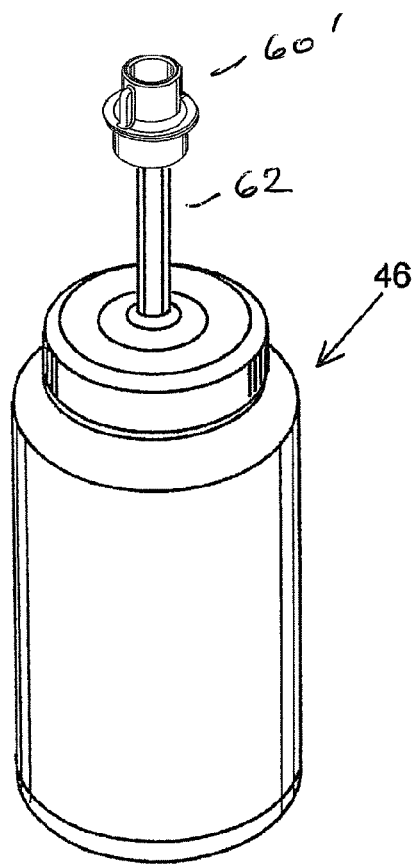
FIG. 7 shows a perspective view of an embodiment of the liquid flushing container of the ostomy bag

The ostomy bag 10 may comprise an internal irrigation system 30 that links to an external water or liquid source and provides for the flushing of the internal components of the ostomy bag, such as the outer chamber upper portion 14, the lower portion 16, and the inner chamber 18. The irrigation system 30 may comprise an irrigation connector adapter 34 which may penetrate front member 2 as shown in FIG. 1. Alternatively, an attachment adapter 36 may be attached to the inside wall of front member 2 as shown in FIG. 2. Attachment adapter 36 may connect directly to a matching connector on vent housing 48 or to a external connector 60, 60' as indicated in FIGS. 5-7. Alternatively, attachment adapter 36 may attach to the irrigation connector adapter 34 as shown in FIG. 1.

As further shown in FIG. 2, the attachment adapter 36 may have a second side which may be attached to an irrigation tube 38 at a back side of the attachment adapter 36. Alternatively the irrigation tube 38 may connect to the irrigation connector adapter 34, and pass through the front member 2 as depicted in FIG. 1. The irrigation tube 38 may be closed-ended, and may be routed through a first slit 40 and a second slit 42 that extend throughout the inner chamber 18 and the outer chamber 12. The irrigation tube 38 may comprise slits 44 along the portion of the irrigation tube 38 that resides within the inner chamber 18 and the lower portion 16 of the outer chamber 12. The slits 44 along the irrigation tube 38 cause the water introduced into the ostomy bag 10 during flushing to disperse from the irrigation tube 38 at a higher pressure.

The water may be introduced into the irrigation tube 38 from a squeezable reservoir 46 of the type shown in FIG. 7, or an alternate embodiment may be used to provide liquids for flushing the ostomy bag 10, such as an adapter which allows connecting a water fixture to irrigation tube 38. Tubing 62 from the irrigation source, such as squeezable reservoir 46 or a faucet, is connected to irrigation connector adapter 34 or to attachment adapter 36 with external connector 60, 60', after vent housing 48 is disconnected from the ostomy bag 10 by releasing the quick release connector. Use of the squeezable reservoir 46 allows the addition of disinfectants or deodorizers to the flushing water to assist in the cleansing of the ostomy bag 10.

Figure 3:
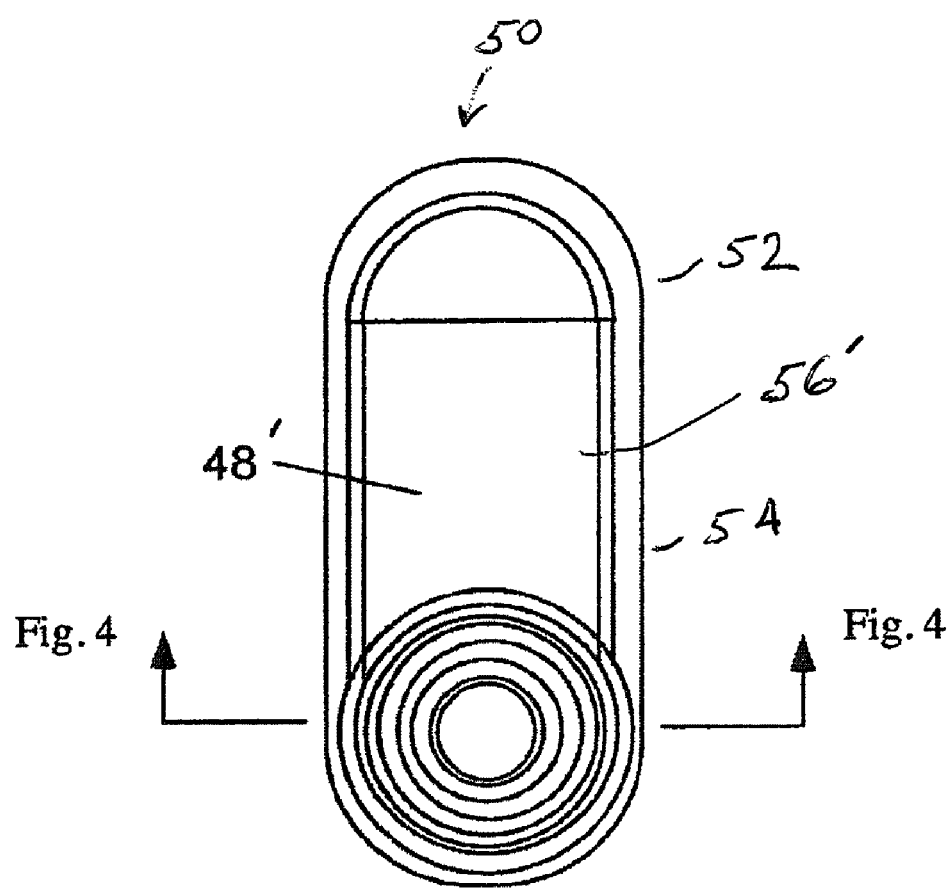
FIG. 3 shows a top view of another embodiment of the filter-connector system.
Figure 4:
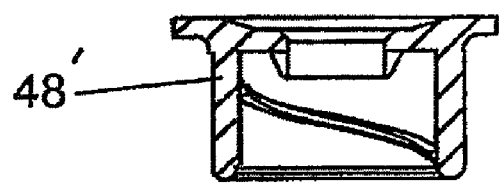
FIG. 4 shows a cross-sectional view of the embodiment of the filter system of FIG. 3, taken essentially along the lines 4-4 of FIG. 3, showing the quick connect structure of the vent housing.

Vent housing 48 is placed at the upper portion 14 of the outer chamber 12, such that the vent housing 48 releases flatus that collects within the bag during normal digestion. The vent housing 48 may mate through the use of mating parts. FIG. 1 shows an embodiment of vent housing 48 in which the filter housing 56 is in axial alignment with the irrigation connector adapter 34. FIGS. 2-3 show embodiments of the vent housing 48' in which the filter housing 56' is at a right angle with irrigation connector adapter 34.

The vent housing 48 is attached and removed from the ostomy bag 10 through the use of a quick disconnect type of attachment, which may attach or releases with a rotation of approximately 180 degrees, where the vent housing is replaced with a connector of an exterior irrigation or cleaning line which is attached to a water supply, such as a squeeze bottle or faucet. The vent housing 48 may further comprise a charcoal filter to strip the noxious smells from the vented flatus. The vent housing 48 may also comprise a liner 50 of either a scent absorbing media, such as a sponge, or liner 50 may comprise a charcoal filter 50. Liner 50 may also be segmented such that a first portion 52 comprises the scent absorbing media while a second portion 54 comprises the charcoal filter. Scents may be added to the scent absorbing media of liner 50.

FIG. 7 shows an embodiment of a squeezable container that may contain fluids utilized for cleaning, sanitizing and deodorizing an ostomy bag by connecting the container via a connection hose 62 to connector 34 or attachment adapter 36, after vent housing 48 has been removed from the connector 34.

While the above is a description of various embodiments of the present invention, further modifications may be employed without departing from the spirit and scope of the present invention. Thus the scope of the invention should not be limited by the specific structures disclosed. Instead the true scope of the invention should be determined by the appended claims.

What is claimed is:

1. An improved ostomy bag, wherein the ostomy bag comprises a waste collection chamber having an interior side and an exterior side, wherein the interior side comprises a first opening for attaching to a user's stoma, the ostomy bag further comprising means for draining the waste, the improvement comprising:
   a second opening on the exterior side, the second opening approximately opposite the first opening;
   an irrigation connector adapter connected to the second opening, the irrigation connector adapter comprising a first quick-connect member for attachment to a corresponding second quick-connect member; and
   a vent housing comprising a first side comprising the second quick connect member, the vent housing comprising a charcoal filter, the vent housing further comprising scent storage means; and
   an irrigation tube adapted to engage the irrigation connector adapter wherein a portion of the irrigation tube comprises slits.

2. The improvement of claim 1 further comprising an attachment adapter affixed to said the exterior side, the attachment adapter affixed to said irrigation connector adapter.

3. The improvement of claim 1 wherein the scent storage means comprises an absorbent medium.

4. The improvement of claim 1 wherein the vent housing defines a first axis and the second quick connect member defines a second axis, and the first axis is in axially alignment with the second axis.

5. The improvement of claim 1 wherein the vent housing defines a first axis and the second quick connect member defines a second axis, and the first axis is normal to the second axis.

6. An improved ostomy bag, wherein the ostomy bag comprises a waste collection chamber having a top and a bottom, wherein the waste collection chamber has an interior side defined by a first peripheral edge and an exterior side defined by a second peripheral edge, the first peripheral edge fused to the second peripheral edge except for a non-fused portion at the bottom defining an opening, the interior side comprising a first inner wall and a first outer wall, and a first opening penetrating through the interior side for attaching to a user's stoma, the outer wall comprising a second inner wall and a second outer wall, the improvement comprising:
   an attachment adapter attached to the second inner wall, the attachment adapter comprising a male connector penetrating the outer wall;
   an irrigation connector adapter connected to the male connector, the irrigation connector adapter comprising a first quick-connect member for attachment to a corresponding second quick-connect member; and
   a vent housing comprising a first side comprising the second quick connect member, the vent housing comprising a charcoal filter, the vent housing further comprising scent storage means; and
   an irrigation tube adapted to engage the irrigation connector adapter wherein a portion of the irrigation tube comprises slits.

7. The improvement of claim 6 wherein the scent storage means comprises an absorbent medium.

8. The improvement of claim 6 wherein the vent housing defines a first axis and the second quick connect member defines a second axis, and the first axis is in axially alignment with the second axis.

9. The improvement of claim 6 wherein the vent housing defines a first axis and the second quick connect member defines a second axis, and the first axis is normal to the second axis.

10. An ostomy bag odor control and irrigation system, the system comprising:
    an ostomy bag comprising a waste collection chamber having a top and a bottom, wherein the waste collection chamber has an interior side defined by a first peripheral edge and an exterior side defined by a second peripheral edge, the first peripheral edge fused to the second peripheral edge except for a non-fused portion at the bottom defining an opening, the interior side comprising a first inner wall and a first outer wall, and a first opening penetrating through the interior side for attaching to a user's stoma, the outer wall comprising a second inner wall and a second outer wall;
    an attachment adapter attached to the second inner wall, the attachment adapter comprising a male connector penetrating the outer wall;
    an irrigation connector adapter connected to the male connector, the irrigation connector adapter comprising a first quick-connect member for attachment to a corresponding second quick-connect member or, alternatively, to a third quick-connect member;
    a vent housing comprising a first side comprising the second quick connect member, the vent housing comprising a charcoal filter, the vent housing further comprising scent storage means;
    a source of irrigation liquid, the source connected to a conduit having the third quick connect member; and
    an irrigation tube adapted to engage the irrigation connector adapter wherein a portion of the irrigation tube comprises slits.

11. The system of claim 10 wherein the scent storage means comprises an absorbent medium.

12. The system of claim 10 wherein the vent housing defines a first axis and the second quick connect member defines a second axis, and the first axis is in axially alignment with the second axis.

13. The system of claim 10 wherein the vent housing defines a first axis and the second quick connect member defines a second axis, and the first axis is normal to the second axis.

14. The system of claim 10 wherein the source of irrigation liquid comprises a squeezable bottle.

* * * * *